United States Patent
Hanna

[11] Patent Number: 5,226,905
[45] Date of Patent: Jul. 13, 1993

[54] INSTRUMENT FOR SURGERY OF THE CORNEA

[76] Inventor: Khalil Hanna, 9 rue du Temple 75007, Paris, France

[21] Appl. No.: 810,133

[22] Filed: Dec. 19, 1991

[30] Foreign Application Priority Data
Dec. 20, 1990 [FR] France .................. 90 16012

[51] Int. Cl.⁵ .................................. A61B 17/32
[52] U.S. Cl. ................... 606/166; 606/161; 606/180
[58] Field of Search .......... 606/4, 5, 161, 166, 606/167, 168, 169, 170, 172, 180; 128/898, 751, 757, 758; 604/22

[56] References Cited

U.S. PATENT DOCUMENTS

| | | | |
|---|---|---|---|
| 4,319,575 | 3/1982 | Bonte | 606/166 |
| 4,429,696 | 2/1984 | Hanna | 606/166 |
| 4,526,171 | 7/1985 | Schachar | 606/166 |
| 4,619,259 | 10/1986 | Graybill et al. | 606/166 |
| 4,688,570 | 8/1987 | Kramer et al. | 606/172 |
| 4,815,463 | 3/1989 | Hanna | 606/166 |
| 4,985,035 | 1/1991 | Torre | 606/167 |

FOREIGN PATENT DOCUMENTS 0248569 9/1987 European Pat. Off. .
2242835 10/1991 United Kingdom ............... 606/166

Primary Examiner—Edgar S. Burr
Assistant Examiner—Christopher A. Bennett
Attorney, Agent, or Firm—Sixbey, Friedman, Leedom & Ferguson

[57] ABSTRACT

The instrument comprises:
a tubular outer support forming a shell about a determined axis and including an annular bottom portion that is circularly symmetrical about the axis to define a substantially spherical annular surface of the support for application against the cornea; and
a tool carrier received inside the outer support and movable relative thereto between a high position and a low position, the tool carrier including a smooth tool-holding socket whose inside wall is resiliently deformable in the radial direction, the socket being axially movable relative to the support, a resilient member disposed between the socket and the support urging the tool carrier towards its high position, and a threaded drive socket screwed into the support above the smooth socket to constitute an adjustable top abutment for the smooth socket and opposing the return effect of the resilient member.

9 Claims, 4 Drawing Sheets

FIG_1

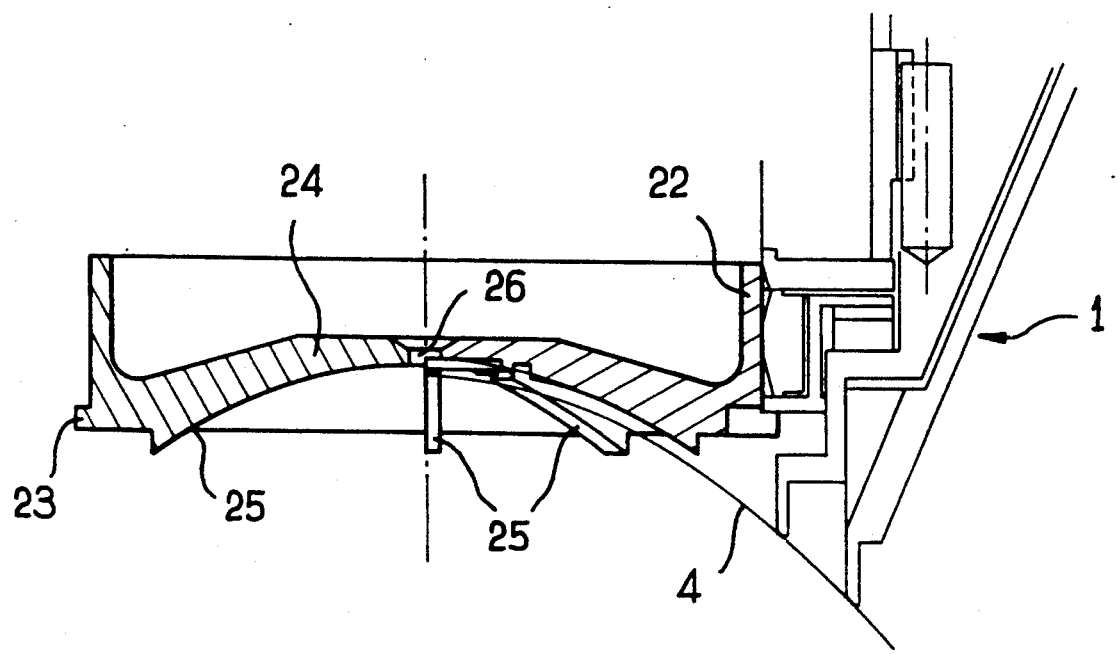
FIG_3
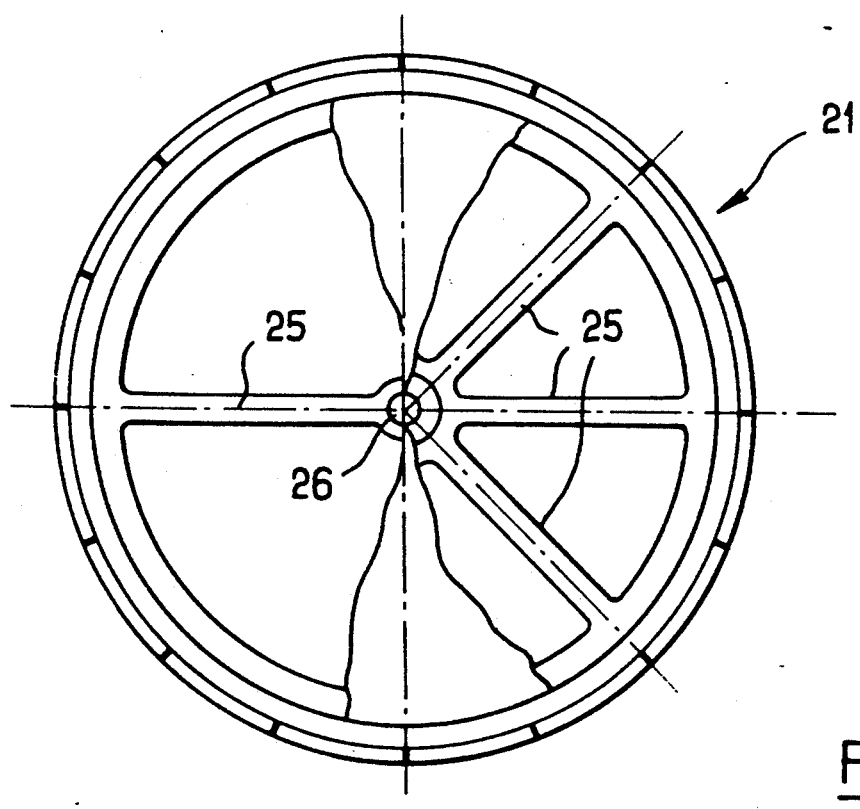
FIG_4

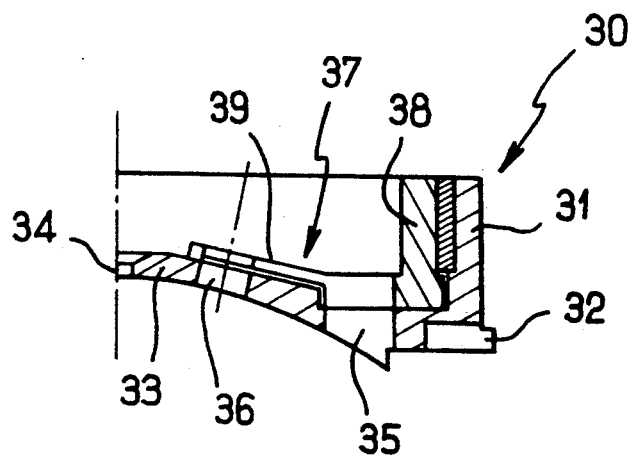
FIG_5
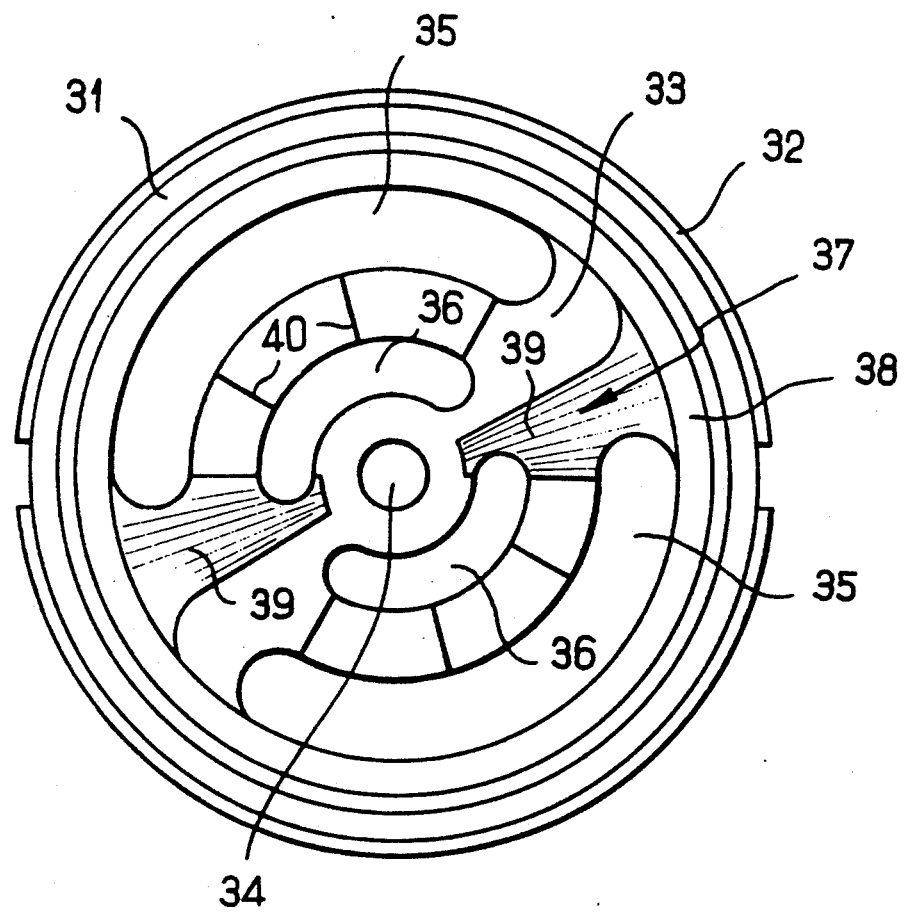
FIG_6

INSTRUMENT FOR SURGERY OF THE CORNEA

BACKGROUND OF THE INVENTION

There exist at present various specialized surgical instruments that the surgeon can use to perform different incisions in the cornea as required by refractive surgery or by trephination of the cornea. Thus, one such keratotomy serves to make radiary incisions for use, in particular, in correcting myopia (short sight). Another is designed to form transverse incisions on one or more meridians of the cornea, preferably in the form of circular arcs, in order to correct astigmatism. An apparatus is also known that is designed to perform trephination of the cornea for transplant purposes.

Although these instruments are extremely effective at performing the operations for which they are designed, there exists an unsatisfied need for equipment that is more simple and that enables a plurality of surgical and presurgical acts to be performed using the same basic equipment. Before making incisions, it is necessary to provide reference marks on the cornea so as to place the surgical instrument correctly firstly relative to the visual axis and second relative to the zones that are to be incised, as dictated by the nature of the disease to be corrected.

The invention seeks to provide a solution to this problem by proposing an instrument having a single body suitable for receiving a plurality of "tools", each being specialized in performing a particular operation.

SUMMARY OF THE INVENTION

To this end, the present invention provides an instrument designed for surgery of the cornea, the instrument comprising:

a tubular outer support forming a shell about a determined axis and including an annular bottom portion that is circularly symmetrical about the axis to define a substantially spherical annular surface of the support for application against the cornea; and a tool carrier received inside the outer support and movable relative thereto between a high position and a low position;

wherein the tool carrier includes a smooth tool-holding socket whose inside wall is resiliently deformable in the radial direction, the socket being axially movable relative to the support, a resilient member disposed between the socket and the support urging the tool carrier towards its high position, and a threaded drive socket screwed into the support above the smooth socket to constitute an adjustable top abutment for the smooth socket and opposing the return effect of the resilient member.

Preferably, the smooth socket includes a radial collar bearing an angular graduation which is adjustable in the position about the axis of the instrument.

To facilitate locating the instrument angularly on the eye of a patient, the threaded socket includes a drive lever extending radially over the outer support.

In addition, the outer support includes a pair of diametrically-opposite handles extending substantially parallel to its longitudinal axis enabling the support to be held by the surgeon, and between which the drive lever is free to move.

With a tool carrier of this type, the tools includes an upper tubular section for fitting in the tool carrier, and a lower outer collar enabling the tool to abut against the tool carrier. This makes it extremely easy to change the tool during an operation (e.g. to switch from a cornea marker to a guide for making incisions).

Thus, one of the tools has a bottom at the base of its tubular portion, which bottom is provided with a central orifice and includes radial ribs projecting downwards from a substantially spherical concave surface. It serves as a marker for the cornea, and depending on the number of ribs it includes, it may serve to perform marking for correcting astigmatism or for making radiary incisions.

Another tool possesses a wall at the base of its tubular portion, which wall is delimited by a spherical outside surface including a central orifice and at least one pair of arcuate slots that are symmetrical about the center of the wall. These slots serve as lateral guides for a knife held in the hand of the surgeon.

Finally, to facilitate the operation and to make it easy to provide accurate incisions, the tool includes a mask for adjusting the angular length of the arcuate openings, the mask being constituted by a tubular sleeve mounted to rotate with friction inside the tubular portion of the tool and including radial wall portions at its base overlying the openings to a greater or lesser extent depending on the angular position of the sleeve in the tubular portion of the tool, while the end wall of the tool includes radial marks for assisting in determining the angular length of the incisions to be made.

BRIEF DESCRIPTION OF THE DRAWINGS

An embodiment of the invention is described by way of example with reference to the accompanying drawings, in which:

FIG. 3 is a section view through a corneal marker fitted to the support of the preceding figures;

FIG. 4 is a plan view of the marker showing two possible variant embodiments; and FIGS. 5 and 6 are respectively an axial half-section and a plan view of a template for making arcuate incisions in the cornea and adapted to be received in the support of FIGS. 1 and 2.

DETAILED DESCRIPTION

Figure 1:
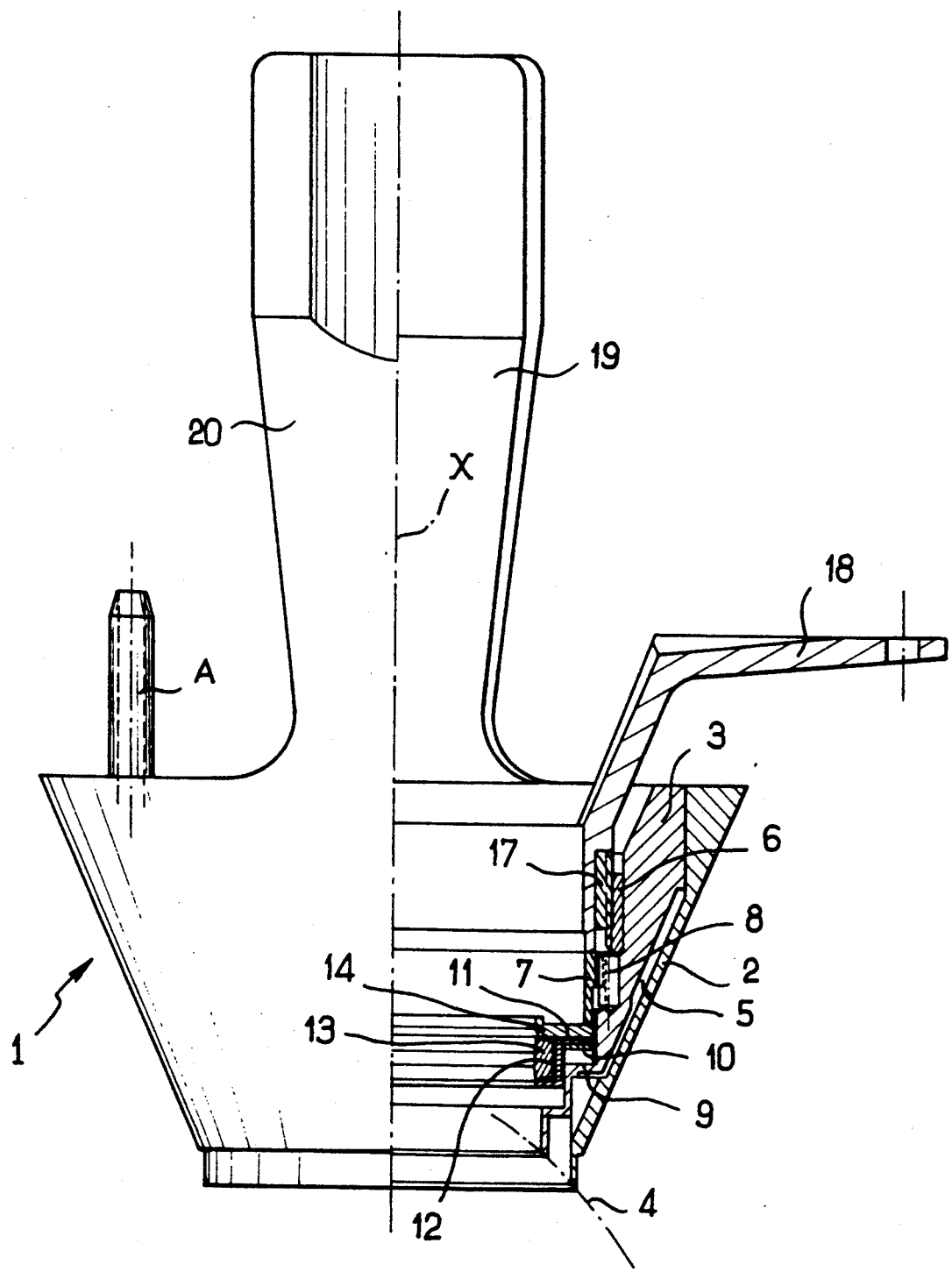
FIG. 1 is an elevation view in axial half-section through the support of an instrument of the invention.
Figure 2:
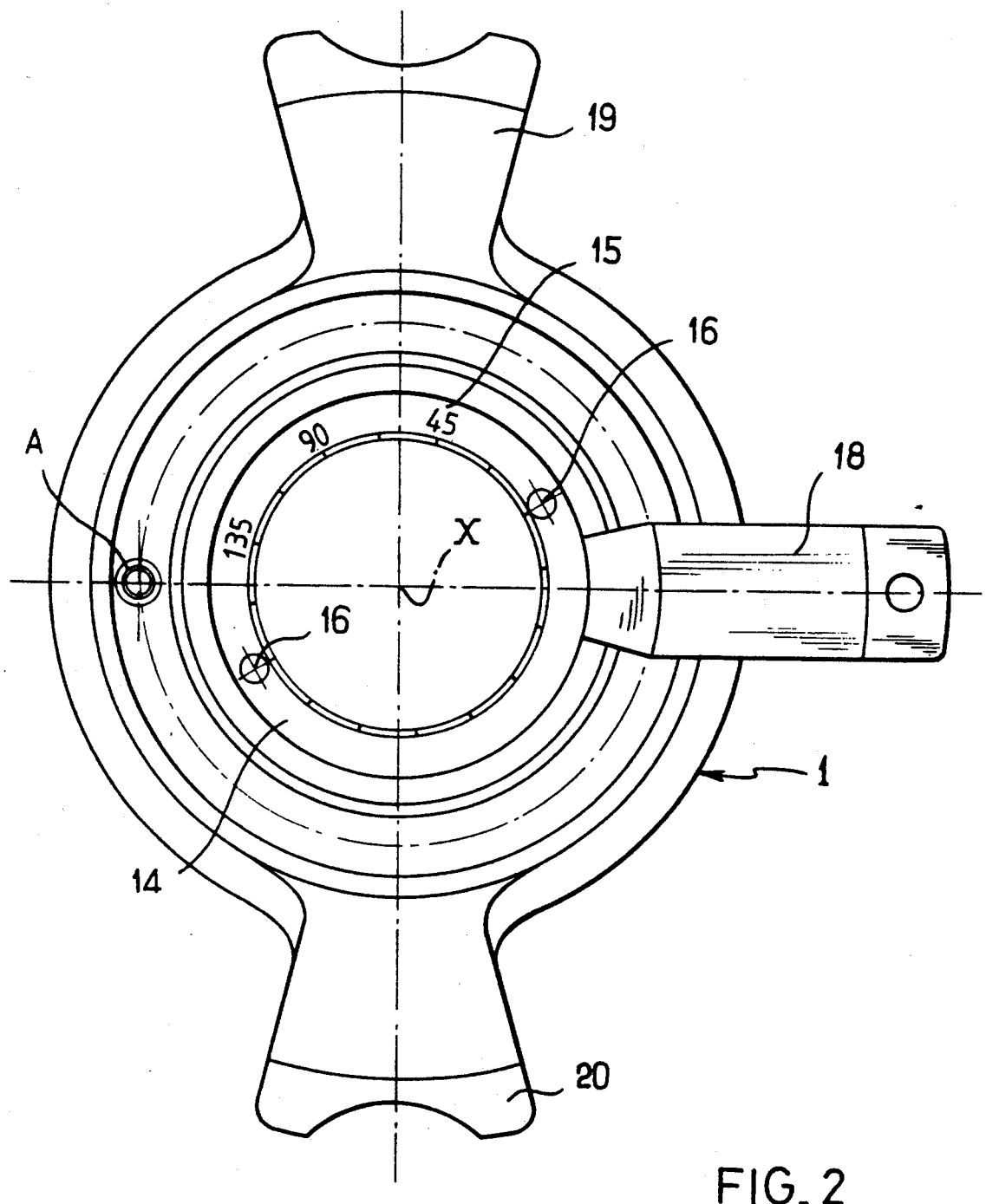
FIG. 2 is a plan view of the support.

The body 1 of the support of the instrument shown in FIGS. 1 and 2 comprises a generally frustoconical outer shell 2 which internally receives a likewise frustoconical complementary part 3 with the two parts being coaxial about an axis X. Together, these two parts define firstly, at the base of their smaller diameter portion (i.e. the bottom portion of the support), an annular surface 4 which is substantially spherical and which constitutes a surface of the instrument for application against the sclera of the eye of a patient, and secondly they define an annular chamber 5 between them, which chamber opens out into the surface 4. This chamber is designed to be connected by means of an endpiece A to a vacuum source whose suction serves to fix the support on the eye of a patient. In a variant of the instrument, the support may be made in a single piece and its bottom portion may include anchoring claws for fixing to the eye of the patient. In another variant, the support may comprise a combination of both fixing techniques.

The inside part 3 of the support is machined on its inside so as to present a plurality of steps. The first step, i.e. the largest-diameter step, receives a tapped sleeve 6.

The sleeve is secured to the support. The cylindrical portion of the next step down constitutes a bearing surface for centering a cylindrical spacer 7 which is capable of sliding axially along said bearing surface but which is prevented from rotating by a key 8. The horizontal shoulder 9 of the next step constitutes a bearing surface for an annular resilient member 10. This resilient member 10 is surmounted by an outer collar 11 of a socket 12 capable of sliding axially along the cylindrical portion of the next step down. This socket 12 is provided with an inside sleeve 13 which is resiliently deformable in a radial direction and into which a specialized tool can therefore be fitted.

The top surface of the collar 11 on the socket 12 includes a ring 14 whose top surface bears angular graduations 15. This ring can be moved angularly by engaging a spike in drive orifices 16.

The instrument support of the invention includes a drive component which is constituted by a socket 17 having an outside thread. This socket thus constitutes a screw which co-operates with the stationary nut 6 and which can thus be moved into the shell of the support. This screw is hollow so as to preserve visual access to the inside of the instrument, and as it rotates it bears on the spacer 7 which, since it is prevented from rotating, transmits only the downwards motion to the smooth socket 12 against the effect of the resilient return member 10 which urges it upwards inside the shell. This spring also retains the socket against any torque tending to cause it to rotate inside the support.

The screw 17 includes a drive lever 18 which extends radially outwards above the frustoconical portion 2, 3 of the support. The support is fitted with handles 19 and 20 of the instrument which extend upwards parallel to its axis.

FIG. 3 shows a portion of the base of the support when fitted with a specialized tool, constituted in this case by a marker 21 for placing geometrical reference marks on the cornea, generally meridians, prior to an operation. Like all instruments that can be received in the support, the marker includes a holding portion in the form of a cylindrical sleeve 22 having an outside diameter such that it fits inside the socket 11, 13 of the support with a small amount of clamping. The bottom portion of the sleeve includes a shoulder 23 which comes into abutment against the bottom portion of the smooth socket 12, thereby accurately determining their relative axial position.

The base of the sleeve is fitted with a bottom wall 24 that is substantially spherical in shape, having a concave bottom surface that includes radial ribs 25 for marking the cornea, with the number of ribs being a function of the operation to be performed. Thus, a marker having eight radial ribs is selected if radiary keratotomy is to be performed. In contrast, a marker having two or four ribs is selected for correcting astigmatism. The wall 24 also includes a central orifice 26 which enables it to be centered relative to the visual axis of the patient.

It will be understood that using the instrument of the invention, it is possible to install the marker in the support in a determined angular position that corresponds to the position determined by the practitioner as a function of the angular position of the apparatus relative to the eye of the patient, which may be indicated by the graduated scale ring. The marker is then retracted above the surface 4 by completely loosening the "screw" 17. The apparatus is put into place and in angular position on the eye of the patient, is held in place by the surgeon and by suction or by claws to prevent sliding, and the screw is driven in such a direction as to lower the marker onto the eye, with the screw pitch and the angular amplitude with which it is screwed in the nut being designed so that at the end of tightening, the ribs have moved past the bearing surface 4 by an appropriate amount.

FIGS. 5 and 6 show a template 30 which like the marker includes an axial sleeve 31 with a shoulder 32 at its base suitable for being fitted in the smooth socket of the support and for being held axially in position within the support. The sleeve 31 also includes a substantially spherical bottom wall 33 provided with a central orifice 34 and at least one pair of diametrically-opposite arcuate slots. In the case shown in the figure, the spherical wall has two pairs of slots, the slots 35 of the first pair having a large mean diameter (e.g. 7 mm or 8 mm), while the slots 36 of the second pair are smaller in diameter (e.g. 5 mm or 6 mm). Their angular extent is identical (about 120°). Their width is equal to the thickness of the surgical micrometer knife that is to be used for making the incisions. The knife may include, for example, a blade carrier having a flat which defines both its width (equal to the width of arcuate slots) and the angular position of the blade.

The template also includes a moving mask 37 which is constituted by a cylindrical tubular portion 38 mounted for braked rotation within the sleeve 31, and diametrically opposite radial fingers 39 which are parallel to the curvature of the wall 33 of the template and of sufficient length to extend past the inside edges of the smaller slots. By rotating the mask relative to the template, the fingers 39 are displaced, which fingers constitute adjustable moving ends for the arcuate slots. The surgeon can thus delimit the length of the incisions that are to be made. Radial marks 40 serve to specify the selected angular length. The surgeon can then locate the middles of the arcs and place the template in the support in such a manner as to make said middles coincide with the selected meridian. The dimensions of the template, and in particular the thicknesses thereof are such that when it is in place on the support, after the part 17 has been tightened, the template projects slightly below the surface 4 so that the cornea is slightly flattened by the bottom face of the template.

I claim:

1. An instrument designed for surgery of the cornea, the instrument comprising:
   a tubular outer support forming a shell about a predetermined axis of the instrument, said tubular outer support including an annular bottom portion that is circularly symmetrical about the axis to define a substantially spherical annular surface of the support for application against the cornea; and
   a tool carrier received inside the outer support and movable relative thereto between a high position and a low position;
   said tool carrier including a smooth tool-holding socket having an inside wall which is resiliently deformable in the radial direction, the socket being axially movable relative to the support along said predetermined axis, a resilient member disposed between the socket and the support urging the tool carrier towards its high position, and a threaded drive socket screwed into the support above the smooth socket to constitute an adjustable top abutment for the smooth socket and opposing the return effect of the resilient member.

2. An instrument according to claim 1, wherein the smooth socket includes a radial collar bearing an angular graduation which is adjustable in the position about the axis of the instrument.

3. An instrument according to claim 1, wherein the threaded socket includes a drive lever extending radially over the outer support.

4. An instrument according to claim 3, wherein the outer support includes a pair of diametrically-opposite handles extending substantially parallel to its longitudinal axis enabling the support to be held by a surgeon, and between which the drive lever is free to move.

5. An instrument according to claim 1, wherein a tool to be positioned in the tool carrier includes an upper tubular section for fitting in the tool carrier, and a lower outer collar for abutting against the tool carrier.

6. An instrument according to claim 5, wherein the tool has a bottom at the base of its tubular portion, which bottom is provided with a central orifice and includes radial ribs projecting downwards from a substantially spherical concave surface.

7. An instrument according to claim 5, wherein the tool includes a wall at the base of its tubular portion, which wall is delimited by a spherical outside surface including a central orifice and at least one pair of arcuate slots that are symmetrical about the center of the wall.

8. An instrument according to claim 7, wherein the tool includes a mask for adjusting the angular length of the arcuate openings, the mask including a tubular sleeve mounted to rotate inside the tubular portion of the tool and including radial wall portions at its base overlying the openings to a varying extend depending on the angular portion of the sleeve in the tubular portion of the tool.

9. An instrument according to claim 7, wherein the wall includes radial marks for determining the angular length of the arcuate incisions to be made.

* * * * *